United States Patent [19]

Shepard

[11] Patent Number: 5,624,418
[45] Date of Patent: Apr. 29, 1997

[54] COLLECTION AND SEPARATION DEVICE

[76] Inventor: R. David Shepard, 38135 Market Sq., Zephyrhills, Fla. 33540

[21] Appl. No.: 539,193

[22] Filed: Oct. 4, 1995

[51] Int. Cl.$^6$ .................................................. A61M 1/00
[52] U.S. Cl. .......................... 604/319; 604/317; 210/85; 210/232; 210/323.1; 210/416.1; 210/443; 210/454; 210/455
[58] Field of Search .................................. 604/319, 414, 604/317; 210/455, 435, 94, 443, 454, 232, 323.1, 85, 416.1

[56] References Cited

U.S. PATENT DOCUMENTS

| | | | |
|---|---|---|---|
| 2,355,620 | 8/1944 | Bower et al. | |
| 3,957,082 | 5/1976 | Fuson et al. | 137/625.41 |
| 4,116,066 | 9/1978 | Mehl et al. | 604/414 |
| 4,643,197 | 2/1987 | Greene et al. | 604/317 |
| 4,809,860 | 3/1989 | Allen | 604/319 |
| 4,957,492 | 9/1990 | McVay | 604/319 |
| 5,493,863 | 2/1996 | Yanagi et al. | 210/444 |
| 5,536,396 | 7/1996 | Mudra et al. | 210/94 |

*Primary Examiner*—Peter A. Hruskoci
*Assistant Examiner*—Betsey J. Morrison
*Attorney, Agent, or Firm*—A. W. Fisher, III

[57] ABSTRACT

A collection and separation device for use in combination with a fluid collection container operatively coupled to a suction source to withdraw body fluids and collect tissue specimens from a patient comprising a tissue collection container operatively coupled between the patient and the fluid collection container having at least one tissue collection basket removably disposed therein to receive body fluids and tissue specimens from the patient including a separator to separate the body fluids and tissue specimens and a fluid collection chamber or zone disposed adjacent the separator such that body fluids and tissue specimens from the patient are received in the tissue collection basket where the body fluids and tissue specimens are separated whereby the tissue specimen is retained in the tissue collection basket for subsequent removal from the tissue collection container and the body fluids are collected in the fluid collection chamber or zone for collection and removal to the fluid collection container.

34 Claims, 2 Drawing Sheets

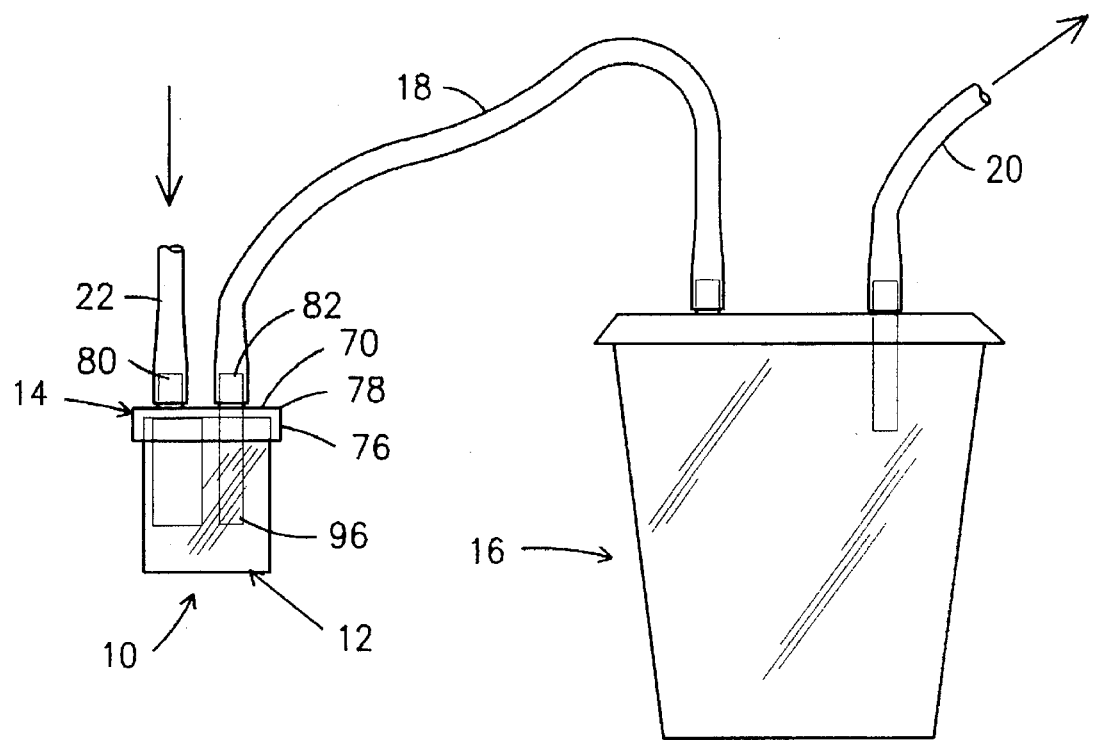
Fig. 1
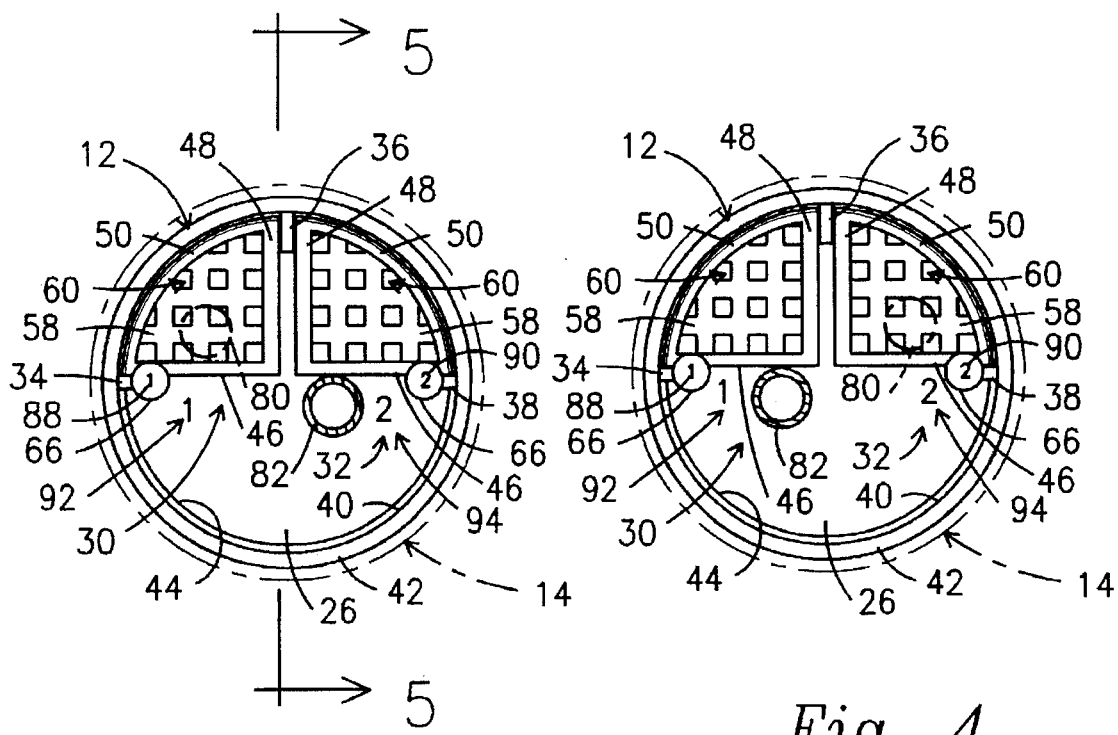
Fig. 3
Fig. 4

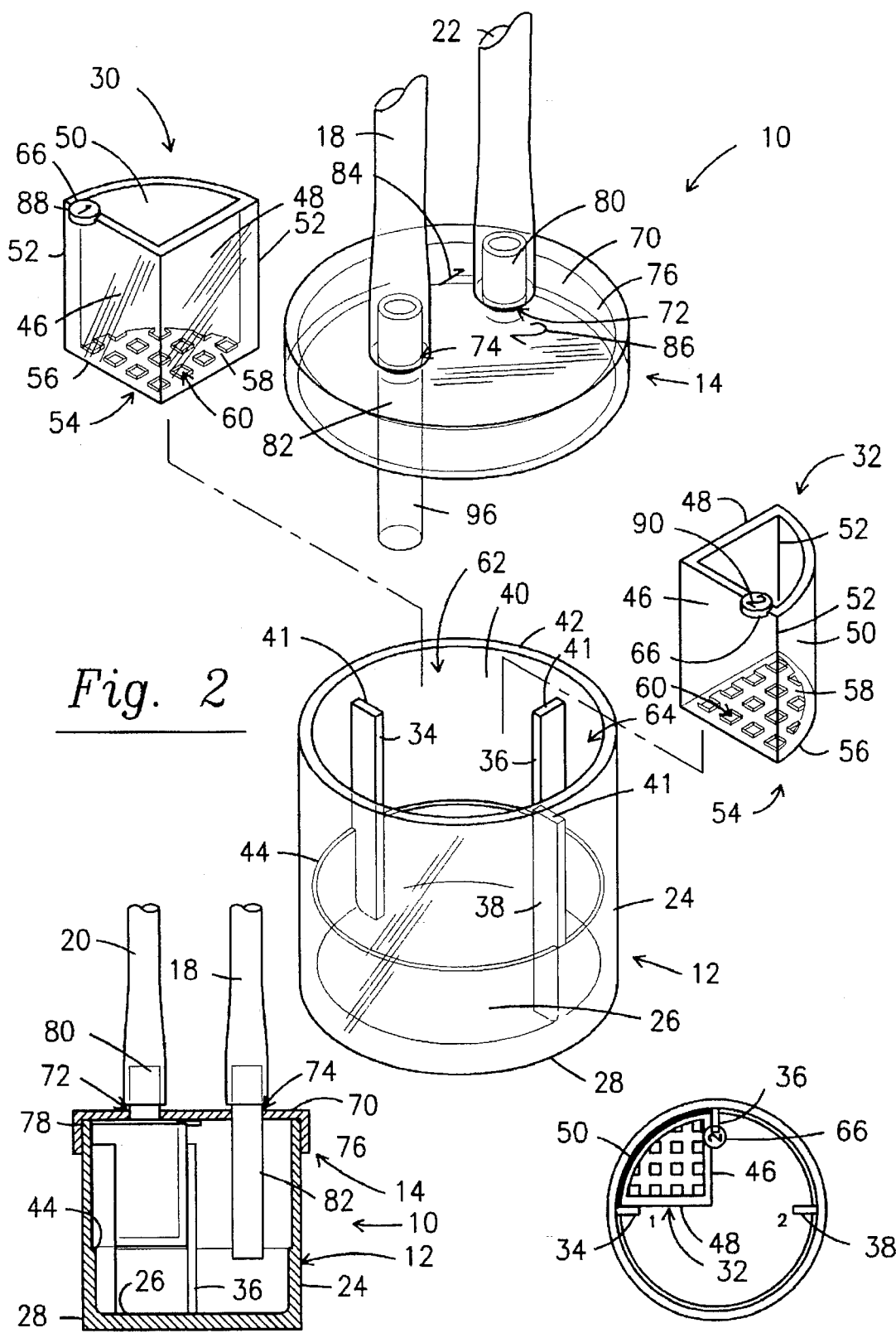

5,624,418

COLLECTION AND SEPARATION DEVICE

BACKGROUND OF THE INVENTION

1. Field of the Invention

A collection and separation device for use with a suction source to withdraw and separate body fluids and tissue specimens from a patient.

2. Description of the Prior Art

Numerous suction collection and drainage devices have been developed to create and enhance drainage from the body of a patient. Some devices may include a collection canister with a disposable liner operatively coupled to a vacuum source. Furthermore, often such devices include a tissue specimen trap connected between the patient and the collection canister to separate the tissue specimen from the body fluid U.S. Pat. No. 4,643,197 describes a suction collection and drainage apparatus comprising a fluid collection container and a tissue specimen trap container connected together to provide fluid communication therebetween. The collection container is connected to a source of suction; while the trap container is connected to an endoscope to permit collection of tissue specimens aspirated from the patient and transmitted to the trap container. A filter having a plurality of traps and a plurality of enlarged openings spaced around the filter. The filter is movable between a first position wherein a selected one of the traps is positioned to receive and collect the tissue specimen and a second position wherein a selected one of the openings is positioned to permit passage therethrough of body fluids when suction is applied to the apparatus.

U.S. Pat. No. 4,957,492 describes a method and apparatus for the collection and handling of pathological tissue specimens during evacuation medical procedures employing a vacuum to draw material from a body cavity into a collection bottle. A tissue trap is used to collect tissue specimens prior to entry of the evacuated material into the collection bottle. The tissue trap can be removed from the system and used as a container for handling and transporting the tissue specimens to avoid contact of the specimens by medical workers during the collection and transport thereof.

U.S. Pat. No. 5,049,273 shows a suction straining apparatus comprising a container having a removable lid including a central web mounted thereon. A vacuum port is formed through the lid to operatively receive a vacuum hose; while, a discharge port is formed through the central web for discharge of fluids from the container. An internally threaded intake port is also formed through the intake web with a straining means mounted thereon to selectively remove particulates from fluid directed through the intake port. The straining means includes a collar member having an upper cylindrical connection collar mounted overlying the central web and a coaxially aligned lower externally and internally threaded cylindrical collar with the lower collar including external threads received within the intake port and a strainer basket mounted to the lower collar.

U.S. Pat. No. 2,355,620 teaches an apparatus comprising a vacuum chamber including a separable body member and a cap member having outlet and inlet conduits supported thereon. The inlet conduit is centrally and rotatably positioned in the cap member with a radially extending nozzle section configured to supply fluid to a plurality of containers concentrically disposed in the body member.

U.S. Pat. No. 2,792,836 describes an apparatus for collecting urine samples comprising a support member having a rotatable member thereon and disposed to support a plurality of removable urinals at angularly spaced intervals thereon. A urine discharge means terminating adjacent the rotatable member is disposed to discharge urine into an adjacent urinal. The apparatus further includes a releasable stop means disposed between the support member and the rotatable member to retain the urinals in succession at a position to receive the urine for a predetermined time interval and means to rotate the rotatable member upon release of the stop means whereby the succeeding urinal is positioned beneath the urine discharge means.

SUMMARY OF THE INVENTION

The present invention relates to a collection and separation device to withdraw and separate body fluids and tissue specimens from a patient and to collect the tissue specimens for subsequent analysis comprising a tissue collection container having a cap removably and rotatably mounted thereon operatively coupled to a vacuum or suction source.

The tissue collection container includes a tissue collection basket retention means formed in the interior thereof to selectively retain a first and second tissue collection basket as body fluids and tissue specimens from the patient are collected and separated in the collection and separation device. A tissue collection basket support ledge extends inward from the inner surface of the tissue collection container to engage and support the first and second tissue collection baskets.

The first and second tissue collection baskets each comprises a tissue collection basket side wall having a separator formed on the lower periphery thereof comprising a member having a plurality of fluid flow apertures formed therethrough to allow body fluids to pass therethrough while retaining the tissue specimens within the first tissue collection basket or the second tissue collection basket.

The collection and separation device further includes a basket positioning means to insure that the first tissue collection basket and the second tissue collection basket are properly positioned in a first tissue collection basket sector and a second tissue collection basket sector. Specifically, a tab or member is formed on the upper edge of each of the first and second tissue collection baskets.

If either the first tissue collection basket or second tissue collection basket is placed in the incorrect tissue collection basket sector, the corresponding tab or member will extend into the other tissue collection basket sector such that the other tissue collection basket would engage the tab or member to prevent placement of the remaining tissue collection basket into the other tissue collection basket sector.

The cap comprises a lid having a fluid/tissue inlet port and a fluid outlet port formed therethrough and a side wall extending downwardly from the outer periphery thereof.

The collection and separation device also includes a visual alignment means to provide a visual indication that the cap, the first tissue collection basket and the second tissue collection basket and the tissue collection container are initially aligned relative to each other.

To operatively assemble the collection and separation device, the first tissue collection basket is positioned within the first tissue collection basket sector and pushed downward to engage the tissue collection basket support ledge. Similarly, the second tissue collection basket is positioned within the second tissue collection basket sector and pushed downward to engage the tissue collection basket support ledge. As previously indicated, the basket positioning means comprising the tabs or members formed on the first and second tissue collection baskets prevents positioning or placement of both the first and second tissue collection baskets in the wrong or incorrect tissue collection basket sectors. The cap is then placed on the tissue collection container. The cap is rotated to align the first tissue collection basket with the fluid/tissue inlet port to receive body fluids and tissue from the patient when suction is applied to the collection and separation device. The body fluids flow through the fluid flow apertures into the lower portion of the tissue collection container; while, the tissue specimens are retained within the first tissue collection basket.

After collection of the tissue specimens in the first tissue collection basket, the cap is rotated to align the second tissue collection basket with the fluid/tissue inlet port to receive body fluids and tissue from the patient when suction is applied to the collection and separation device. The body fluids flow through the plurality of fluid flow apertures into the lower portion of the tissue collection container; while, the tissue specimen are retained in the first tissue collection basket.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 1 is a side view of the collection and separation device of the present invention in combination with a fluid collection container.

FIG. 2 is an exploded perspective view of the collection and separation device of the present invention.

FIG. 3 is a cross-sectional top view of the collection and separation device of the present invention with the cap in the first position.

FIG. 4 is a cross-sectional top view of the collection and separation device of the present invention with the cap in the second position.

FIG. 5 is a cross-sectional side view of the collection and separation device of the present invention taken alone line 5—5 of FIG. 3.

FIG. 6 is a schematic top view of the collection and separation device depicting improper placement of one of the tissue collection baskets.

Similar reference characters refer to similar parts throughout the several views of the drawings.

DETAILED DESCRIPTION OF THE PREFERRED EMBODIMENT

As shown in FIGS. 1, 2 and 5, the present invention relates to a collection and separation device generally indicated as 10 to withdraw and separate body fluids and tissue specimens from a patient and to collect the tissue specimens for subsequent analysis. The collection and separation device 10 comprises a tissue collection container generally indicated as 12 having a cap generally indicated as 14 removably and rotatably mounted thereon operatively coupled to a vacuum or suction source (not shown) through a fluid collection container generally indicated as 16 by a fluid conduit 18 connected between the collection and separation device 10 and the fluid collection container 16 and a vacuum conduit 20 connected between the fluid collection container 16 and the vacuum or suction source (not shown) as described more fully hereinafter. Further, the collection and separation device 10 is coupled to the patient through a fluid/tissue conduit 22 as described more fully hereinafter.

As best shown in FIGS. 2 through 5, the tissue collection container 12 comprises a substantially cylindrical side wall 24 and a circular bottom wall 26 formed on the lower periphery 28 thereof. A tissue collection basket retention means is formed in the interior of the tissue collection container 12 to selectively retain a first tissue collection basket and a second tissue collection basket generally indicated as 30 and 32 respectively as body fluids and tissue specimens from the patient are collected and separated in the collection and separation device 10. More specifically, the tissue collection basket retention means comprises a first, an intermediate and a second vertically disposed spaced apart substantially parallel rib indicated as 34, 36 and 38 respectively extending inwardly from the inner surface 40 of the substantially cylindrical side wall 24. The upper ends of the first, intermediate and second vertically spaced apart substantially parallel ribs 34, 36 and 38 each indicated as 41 are spaced below the upper periphery 42 of the substantially cylindrical side wall 24. In addition, a tissue collection basket support ledge 44 extends inward from the inner surface 40 of the substantially cylindrical side wall 24 in spaced relationship relative to the upper ends 41 of the first, intermediate and second vertically disposed spaced apart substantially parallel ribs 34, 36 and 38 to engage and support the first and second tissue collection baskets 30 and 32 as described more fully hereinafter.

As best shown in FIGS. 2 through 4, the first and second tissue collection baskets 30 and 32 each comprises a tissue collection basket side wall including a substantially flat first wall section 46 and a substantially flat second wall section 48 disposed in substantially perpendicular relationship relative to each other and an arcuate wall section 50 extending between the outer edges 52 of the substantially flat first and second wall sections 46 and 48 and a separator generally indicated as 54 formed on the lower periphery 56 of the tissue collection basket side wall. When the collection and separation device 10 is properly assembled, the substantially flat first wall section 46 of the first and second tissue collection basket 30 and 32 are disposed in substantially the same place relative to each other and engage the first and third vertically disposed ribs 34 and 38 respectively; while, the substantially flat second wall section 48 of the first and second tissue collection basket 30 and 32 are disposed in substantially parallel relative to each other and engage opposite sides of the vertically disposed second rib 36. The separator 54 comprises a member 58 having a plurality of fluid flow apertures each indicated as 60 formed therethrough to allow body fluids to pass therethrough while retaining the tissue specimens within the first tissue collection basket 30 or the second tissue collection basket 32 as described more fully hereinafter.

The collection and separation device 10 further includes a basket positioning means to insure that the first tissue collection basket 30 and the second tissue collection basket 32 are properly positioned in a first tissue collection basket sector 62 and a second tissue collection basket sector 64 respectively. The first tissue collection basket sector 62 is cooperatively formed by the vertically disposed first rib 34 and the vertically disposed second rib 36 while the second tissue collection basket sector 64 is formed by the vertically disposed second rib 36 and the vertically disposed third rib 38. Specifically, a tab or member 66 is formed on the upper edge 68 of the substantially flat first wall section 46 of each of the first and second tissue collection baskets 30 and 32 adjacent the respective arcuate wall section 50.

As shown in FIG. 6, if either the first tissue collection basket 30 or second tissue collection basket 32 is placed in the incorrect tissue collection basket sector 62/64, the corresponding tab or member 66 will extend over the upper end 41 of the vertically disposed second rib 36 into the other tissue collection basket sector 62/64 such that the other tissue collection basket 30/32 would engage the tab or member 66 to prevent placement of the remaining tissue collection basket 30/32 into the other tissue collection basket sector 62/64.

As best shown in FIGS. 1, 2 and 5, the cap 14 comprises a substantially circular flat lid 70 having a fluid/tissue inlet port 72 and a fluid outlet port 74 formed therethrough and a substantially cylindrical side wall 76 extending downwardly from the outer periphery 78 thereof. A substantially rigid fluid/tissue inlet tube 80 axially aligned with the fluid/tissue inlet port 72 extends upwardly from the substantially circular flat lid 70 to operatively receive the fluid/tissue conduit 22 thereon; while, a substantially rigid fluid outlet tube 82 extends through the fluid outlet port 74 into the tissue collection container 12 to operatively receive the fluid conduit 18 thereon.

The lower portion of the substantially rigid fluid outlet tube 82 and the substantially flat first wall section 46 of the first and second tissue collection baskets 30 and 32 cooperatively form a tissue collection basket alignment means as described more fully hereinafter.

The collection and separation device 10 also includes a visual alignment means to provide a visual indication that the cap 14, the first tissue collection basket 30 and the second tissue collection basket 32, and the tissue collection container 12 are initially aligned relative to each other.

Specifically, a first and second cap indicia as the numerals 1 and 2 or letters A and B indicated as 84 and 86 respectively are formed on the substantially circular flat lid 70 as best shown in FIG. 2, a corresponding first and second basket indicia such as the numerals 1 and 2 or letters A and B indicated as 88 and 90 respectively formed on the tabs or members 66 on the first and second tissue collection baskets respectively as best shown in FIGS. 3 and a first and second sector indicia as numerals 1 and 2 or letters A and B indicated as 92 and 94 respectively formed on the circular bottom wall 26 of the tissue collection container 12 as best shown in FIGS. 3 and 4.

To operatively assemble the collection and separation device 10, the first tissue collection basket 30 bearing the first basket indicia 88 corresponding to the first sector indicia 92 is positioned within the first tissue collection basket sector 62 and pushed downward to engage the tissue collection basket support ledge 44. Similarly, the second tissue collection basket 32 bearing the second basket indicia 90 corresponding to the second sector indicia 94 is positioned within the second tissue collection basket sector 64 and pushed downward to engage the tissue collection basket support ledge 44. As previously indicated, the basket positioning means comprising the tabs or members 66 formed on the upper ledge 68 of the substantially flat first wall sections 46 of the first and second tissue collection baskets 30 and 32 prevents positioning or placement of both the first and second tissue collection baskets 30 and 32 in the wrong or incorrect tissue collection basket sectors 62/64. The cap 14 is then placed on the tissue collection container 12. The cap 14 is rotated to align the first cap indicia 84 with the first basket indicia 88 and the first sector indicia 92 such that the first tissue collection basket 30 is aligned with the lower end of the substantially rigid fluid/tissue inlet tube 80 to receive body fluids and tissue from the patient through the fluid/tissue conduit 22 when suction is applied to the collection and separation device 10 through the vacuum conduit 20, fluid collection container 16 and fluid conduit 18. The body fluids flow through the fluid flow apertures 60 into the lower portion of the tissue collection container 12; while, the tissue specimens are retained within the first tissue collection basket 30.

After collection of the tissue specimens in the first tissue collection basket 30, the cap 14 is rotated to align the second cap indicia 86 with the second basket indicia 90 and the second sector indicia 94 such that the second tissue collection basket 32 is aligned with the lower end of the substantially rigid fluid/tissue inlet tube 80 to receive body fluids and tissue from the patient through the fluid/tissue conduit 22 when suction is applied to the collection and separation device 10 through the vacuum conduit 20, the fluid collection container 16 and fluid conduit 18. The body fluids flow through the plurality of fluid flow apertures 60 into the lower portion of the tissue collection container 12; while, the tissue specimen are retained in the first tissue collection basket 30.

The collection and separation device 10 further includes a rotational limit means to limit the rotational movement of the cap 14 relative to the tissue collection container 12 to selectively align the substantially rigid fluid/tissue inlet tube 80 relative to the first tissue collection basket 30 or the second tissue collection basket 32. Specifically, the lower portion or member 96 of the substantially rigid fluid outlet tube 82 is disposed to engage the substantially flat first wall section 46 of the second tissue collection basket 32 when the substantially rigid fluid/tissue inlet tube 80 is vertically aligned with the first tissue collection basket 30 and to engage the substantially flat first wall section 46 of the first tissue collection basket 30 when the substantially rigid fluid/tissue inlet tube 80 is vertically aligned with the second tissue collection basket 32.

Once the tissue specimens have collected and separated from the body fluids, the cap 14 is removed from the tissue collection container 12 allowing removal of the first tissue collection basket 30 and the second tissue collection basket 32 therefrom.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A collection and separation device for use in combination with a fluid collection container operatively coupled to a suction source to withdraw body fluids and collect tissue specimens from a patient comprising a tissue collection container operatively coupled between the patient and the fluid collection container having a first tissue collection basket removably disposed therein to receive body fluids and tissue specimens from the patient including a separator to separate the body fluids and tissue specimens such that body fluids and tissue specimens from the patient are received in said first tissue collection basket where specimens are separated whereby tissue specimens are retained in said first tissue collection basket for subsequent removal from said tissue collection container and the body fluids are collected in the fluid collection chamber, said collection and separation device further including a first tissue collection basket retention means comprising a first and second substantially vertically disposed spaced apart substantially parallel ribs extending inwardly from the inner surface of said tissue collection container to cooperatively form a first tissue collection basket sector to selectively retain said first tissue collection basket therein.

2. The collection and separation device of claim 1 further including a second tissue collection basket retention means formed in the interior of said tissue collection container to selectively retain a second tissue collection basket therein, said second tissue collection basket retention means comprises said second and a third vertically disposed spaced apart substantially parallel rib extending inwardly from the inner surface of said tissue collection container to cooperatively form a second tissue collection basket sector to receive said second tissue collection basket therein.

3. The collection and separation device of claim 2 wherein said separator comprises a member having a plurality of fluid flow apertures formed therethrough to allow body fluids to pass therethrough while retaining the tissue specimens within said first tissue collection basket or said second tissue collection basket.

4. The collection and separation device of claim 2 wherein said tissue collection container further includes a tissue collection basket support to engage said first and second tissue collection baskets when disposed in said first and second tissue collection basket sectors respectively.

5. The collection and separation device of claim 2 further including a basket positioning means to position said first tissue collection basket and said second collection basket in said first tissue collection basket sector and said second tissue collection basket sector respectively.

6. The collection and separation device of claim 5 wherein said basket positioning means comprises a member formed on each of said first and second tissue collection baskets such that if either said first tissue collection basket or said second tissue collection basket is placed in the incorrect tissue collection basket sector, said corresponding member will extend into said other tissue collection basket sector whereby said other tissue collection basket engages said member to prevent placement of said remaining tissue collection basket into said other tissue collection basket sector.

7. The collection and separation device of claim 2 wherein each said first and second tissue collection basket comprises a tissue collection basket side wall including a first wall section and a second wall section and an arcuate wall section extending between the outer edges of said first and second wall sections and a separator formed on the lower periphery of said tissue collection basket side wall.

8. The collection and separation device of claim 7 wherein said first wall sections of said first and said second tissue collection basket are disposed to engage said first and third vertically disposed ribs respectively; and said second wall sections of said first and said second tissue collection basket are disposed to engage opposite sides of said second vertically disposed rib.

9. The collection and separation device of claim 7 further including a cap comprising a lid having a fluid/tissue inlet port formed therethrough to selectively feed body fluid and tissue specimens from the patient into the interior of said tissue collection container.

10. The collection and separation device of claim 9 further including a rotational limit means to limit the rotational movement of said cap relative to said tissue collection container to selectively align said fluid/tissue inlet relative with said first tissue collection basket or said second tissue collection basket.

11. The collection and separation device of claim 10 wherein said rotational limit means comprises a member extending downwardly from said lid to engage said first wall section of said second tissue collection basket when said fluid/tissue inlet is aligned with said first tissue collection basket and to engage said first wall section of said first tissue collection basket when said fluid/tissue inlet is aligned with said second tissue collection basket.

12. The collection and separation device of claim 9 further including a visual alignment means further includes a first and second cap indicia formed on said lid corresponding and a first and second sector indicia formed on said tissue collection container to provide a visual indicia that said cap and said tissue collection container are properly aligned.

13. The collection and separation device of claim 7 further including a basket positioning means to position said first tissue collection basket and said second tissue collection basket in said first tissue collection basket sector and said second tissue collection basket sector respectively.

14. The collection and separation device of claim 13 wherein said basket positioning means comprises a member formed on said first wall section of each of said first and said second tissue collection baskets adjacent said respective arcuate wall section such that if either said first tissue collection basket or said second tissue collection basket is placed in the incorrect tissue collection basket sector, said corresponding member will extend into said other tissue collection basket sector whereby said other tissue collection basket engages said member to prevent placement of said remaining tissue collection basket into said other tissue collection basket sector.

15. The collection and separation device of claim 13 further including a visual alignment means to provide a visual indication that said first tissue collection basket and second tissue collection baskets are properly aligned relative to said first tissue collection basket sector and said second tissue collection basket sector respectively.

16. The collection and separation device of claim 15 wherein said visual alignment means comprises a first and second basket indicia formed on said first and second tissue collection basket respectively and a first and second sector indicia formed on said tissue collection container corresponding to said first and second basket indicia respectively.

17. The collection and separation device of claim 16 wherein said visual alignment means further includes a first and second cap indicia formed on said lid corresponding to said first and second basket indicia respectively and said first and second sector indicia respectively to provide a visual indication that said cap, said first and second tissue collection baskets and said tissue collection containers are properly aligned.

18. A collection and separation device for use in combination with a fluid collection container operatively coupled to a suction source to withdraw body fluids and collect tissue specimens from a patient comprising a tissue collection container operatively coupled between the patient and the fluid collection container having a first and second tissue collection basket removably disposed therein to receive body fluids and tissue specimens from the patient including a separator to separate the body fluids and tissue specimens, a first tissue collection basket retention means formed in the interior of said tissue collection container to selectively retain said first tissue collection basket within a first tissue collection basket sector formed therein and a second tissue collection basket retention means formed in the interior of said tissue collection container to selectively retain said second tissue collection basket within a second tissue collection basket sector formed therein, said collection and separation device further including a cap comprising a lid having a fluid/tissue inlet port formed therethrough to selectively feed body fluid and tissue specimens from the patient into the interior of said tissue collection container and a rotational limit means to limit the rotational movement of said cap relative to said tissue collection container to selectively align said fluid/tissue inlet relative with said first tissue collection basket or said second tissue collection basket.

19. The collection and separation device of claim 18 wherein said rotational limit means comprises a member extending downwardly from said lid to engage said second tissue collection basket when said fluid/tissue inlet is aligned with said first tissue collection basket and to engage said first tissue collection basket when said fluid/tissue inlet is aligned with said second tissue collection basket.

20. The collection and separation of claim 18 further including a visual alignment means further includes a first and second cap indicia formed on said lid corresponding and a first and second sector indicia formed on said tissue collection container to provide a visual indicia that said cap and said tissue collection container are properly aligned.

21. The collection and separation device of claim 18 wherein said tissue collection container further includes a tissue collection basket support to engage said first and second tissue collection baskets when disposed in said first and second tissue collection basket sectors respectively.

22. The collection and separation device of claim 18 further including a basket positioning means to position said first tissue collection basket and said second tissue collection basket in said first tissue collection basket sector and said second tissue collection basket sector respectively.

23. The collection and separation device of claim 22 wherein said basket positioning means comprises a member formed on each of said first and said second tissue collection baskets such that if either said first tissue collection basket or said second tissue collection basket is placed in the incorrect tissue collection basket sector, said corresponding member will extend into said other tissue collection basket sector whereby said other tissue collection basket engages said member to prevent placement of said remaining tissue collection basket into said other tissue collection basket sector.

24. The collection and separation device of claim 18 further including a visual alignment means to provide a visual indication that said first tissue collection basket and second tissue collection baskets are properly aligned relative to said first tissue collection basket sector and said second tissue collection basket sector respectively.

25. The collection and separation device of claim 24 wherein said visual alignment means comprises a first and second basket indicia formed on said first and second tissue collection basket respectively and a first and second sector indicia formed on said tissue collection container corresponding to said first and second basket indicia respectively.

26. The collection and separation device of claim 25 wherein said visual alignment means further includes a first and second cap indicia formed on said lid corresponding to said first and second basket indicia respectively and said first and second sector indicia respectively to provide a visual indication that said cap, said first and second tissue collection baskets and said tissue collection containers are properly aligned.

27. A collection and separation device for use in combination with a fluid collection container operatively coupled to a suction source to withdraw body fluids and collect tissue specimens from a patient comprising a tissue collection container operatively coupled between the patient and the fluid collection container having a first and second collection basket removably disposed therein to receive body fluids and tissue specimens from the patient including a separator to separate the body fluids and tissue specimens such that body fluids and tissue specimens from the patient are selectively received in said first and second tissue collection baskets where the body fluids and tissue specimens are separated whereby tissue specimens are retained in said first and second tissue collection baskets for subsequent removal from said tissue collection container and the body fluids are collected in the fluid container chamber, said collection and separation device further including first tissue collection basket retention means formed in the interior of said tissue collection container to selectively retain said first tissue collection basket within a first tissue collection basket sector formed therein and a second tissue collection basket retention means formed in the interior of said tissue collection container to selectively retain said second tissue collection basket within a second tissue collection basket sector formed therein and a basket positioning means to position said first tissue collection basket and said second tissue collection basket in said first tissue collection basket sector and said second tissue collection basket sector respectively, said basket positioning means comprises a member formed on a wall section of each of said first and said second tissue collection baskets such that if either said first tissue collection basket or said second tissue collection basket is placed in the incorrect tissue collection basket sector, said corresponding member will extend into said other tissue collection basket sector whereby said other tissue collection basket engages said member to prevent placement of said remaining tissue collection basket into said other tissue collection basket sector.

28. A collection and separation device for use in combination with a fluid collection container operatively coupled to a suction source to withdraw body fluids and collect tissue specimens from a patient comprising a tissue collection container operatively coupled between the patient and the fluid collection container having a first and second tissue collection basket removable disposed therein to receive body fluids and tissue specimens from the patient including a separator to separate the body fluids and tissue specimens such that body fluids and tissue specimens from the patient are selectively received in said first and second tissue collection baskets where the body fluids and tissue specimens are separated whereby tissue specimens are retained in said first and second tissue collection baskets for subsequent removal from said tissue collection container and the body fluids are collected in the fluid collection chamber, said collection and separation device further including a first tissue collection basket retention means formed in the interior of said tissue collection container to selectively retain said first tissue collection basket within a first tissue collection basket sector formed therein and a second tissue collection basket retention means formed in the interior of said tissue collection container to selectively retain said second tissue collection basket within a second tissue collection basket sector formed therein and a visual alignment means to provide a visual indication that said first tissue collection basket and second tissue collection baskets are properly aligned relative to said first tissue collection basket sector and said second tissue collection basket sector respectively.

29. The collection and separation device of claim 28 wherein said visual alignment means comprises a first and second basket indicia formed on said first and second tissue collection basket respectively and a first and second sector indicia formed on said tissue collection container corresponding to said first and second basket indicia respectively.

30. The collection and separation device of claim 29 wherein said visual alignment means further includes a first and second cap indicia formed on said lid corresponding to said first and second basket indicia respectively and said first and second sector indicia respectively to provide a visual indication that said cap, said first and second tissue collection baskets and said tissue collection containers are properly aligned.

31. The collection and separation device of claim 29 further including a visual alignment means further includes a first and second cap indicia formed on said lid corresponding and a first and second sector indicia formed on said tissue collection container to provide a visual indicia that said cap and said tissue collection container are properly aligned.

32. A collection and separation device for use in combination with a fluid collection container operatively coupled to a suction source to withdraw body fluids and collect tissue specimens from a patient comprising a tissue collection container operatively coupled between the patient and the fluid collection container having a first and second tissue collection basket removable disposed therein to receive body fluids and tissue specimens from the patient including a separator to separate the body fluids and tissue specimens such that body fluids and tissue specimens from the patient are selectively received in said first and second tissue collection baskets where the body fluids and tissue specimens are separated whereby tissue specimens are retained in said first and second tissue collection baskets for subsequent removal from said tissue collection container and the body fluids are collected in the fluid collection chamber, said collection and separation device further including a first tissue collection basket retention means formed in the interior of said tissue collection container to selectively retain said first tissue collection basket within a first tissue collection basket sector formed therein and a second tissue collection basket retention means formed in the interior of said tissue collection container to selectively retain said second tissue collection basket within a second tissue collection basket sector formed therein and a tissue collection basket support to engage said first and second tissue collection baskets when disposed in said first and second tissue collection basket sectors respectively.

33. A collection and separation device for use in combination with a fluid collection container operatively coupled to a suction source to withdraw body fluids and collect tissue specimens from a patient comprising a tissue collection container operatively coupled between the patient and the fluid collection container having a first and second collection basket removably disposed therein to receive body fluids and tissue specimens from the patient including a separator to separate the body fluids and tissue specimens such that body fluids and tissue specimens from the patient are selectively received in said first and second tissue collection baskets where the body fluids and tissue specimens are separated whereby tissue specimens are retained in said first and second tissue collection baskets for subsequent removal from said tissue collection container and the body fluids are collected in the fluid container chamber, said collection and separation device further including first tissue collection basket retention means formed in the interior of said tissue collection container to selectively retain said first tissue collection basket within a first tissue collection basket sector formed therein and a second tissue collection basket retention means formed in the interior of said tissue collection container to selectively retain said second tissue collection basket within a second tissue collection basket sector formed therein and a basket positioning means to position said first tissue collection basket and said second tissue collection basket in said first tissue collection basket sector and said second tissue collection basket sector respectively.

34. The collection and separation device of claim 33 wherein said basket positioning means comprises a member formed on a wall section of each of said first and said second tissue collection baskets such that if either said first tissue collection basket or said second tissue collection basket is placed in the incorrect tissue collection basket sector, said corresponding member will extend into said other tissue collection basket sector whereby said other tissue collection basket engages said member to prevent placement of said remaining tissue collection basket into said other tissue collection basket sector.

* * * * *